United States Patent
Song et al.

(10) Patent No.: US 11,096,967 B2
(45) Date of Patent: Aug. 24, 2021

(54) PHARMACEUTICAL COMPOSITION FOR PREVENTING OR TREATING REGULATORY T CELL-MEDIATED DISEASES

(71) Applicant: SCM LIFESCIENCE CO., LTD., Incheon (KR)

(72) Inventors: Sun Uk Song, Incheon (KR); Tac Ghee Yi, Yangju-si (KR); Hyun Joo Lee, Bucheon-si (KR)

(73) Assignee: SCM LIFESCIENCE CO., LTD., Incheon (KR)

( * ) Notice: Subject to any disclaimer, the term of this patent is extended or adjusted under 35 U.S.C. 154(b) by 0 days.

(21) Appl. No.: 16/069,486

(22) PCT Filed: Feb. 24, 2017

(86) PCT No.: PCT/KR2017/002096
§ 371 (c)(1),
(2) Date: Jul. 11, 2018

(87) PCT Pub. No.: WO2017/146538
PCT Pub. Date: Aug. 31, 2017

(65) Prior Publication Data
US 2019/0022144 A1    Jan. 24, 2019

(30) Foreign Application Priority Data
Feb. 26, 2016 (KR) .................. 10-2016-0023551

(51) Int. Cl.
*A61K 35/28* (2015.01)
*A61P 1/00* (2006.01)
*C12N 5/0783* (2010.01)
*C12N 15/85* (2006.01)

(52) U.S. Cl.
CPC .............. *A61K 35/28* (2013.01); *A61P 1/00* (2018.01); *C12N 5/0637* (2013.01); *C12N 15/85* (2013.01); *C12N 2501/2301* (2013.01); *C12N 2501/2302* (2013.01); *C12N 2501/2306* (2013.01); *C12N 2501/25* (2013.01); *C12N 2501/90* (2013.01); *C12N 2506/11* (2013.01)

(58) Field of Classification Search
CPC .. A61K 35/28; C12N 5/0637; C12N 2506/11; C12N 2501/90; C12N 2501/25; C12N 2501/2306; C12N 2501/2302; C12N 2501/2301
See application file for complete search history.

(56) References Cited

U.S. PATENT DOCUMENTS 10,072,079 B2 *  9/2018  Ehninger ............ C07K 16/2803
2013/0071409 A1 *  3/2013  Riley .................... A61K 35/17
                                                              424/172.1

FOREIGN PATENT DOCUMENTS

JP        05900865 B        3/2016

OTHER PUBLICATIONS

Mohammadpour et al., TNF-α modulates the immunosuppressive effects of MSCs on dendritic cells and T cells. International Immunopharmacology, vol. 28, No. 2 (Oct. 2015) pp. 1009-1017. (Year: 2015).*
Sakaguchi, S. et al., "Immunologic self-tolerance maintained by activated T cells expressing IL-2 receptor alpha-chains (CD25)," The Journal of Immunology, vol. 155, No. 3, pp. 1151-1164, Aug. 1, 1995.
Gershon, R. K. and K. Kondo, "Cell Interactions in the Induction of Tolerance: The Role of Thymic Lymphocytes," Immunology, vol. 18, pp. 723-737, 1970.
Iwata, Ryoichi et al., "IT-14, Mesenchymal Glioma Stem Cell Express ICOS," Neuro-Oncology, vol. 16, 2014. Abstract.
Busse, Mandy et al., "ICOS Mediates the Generation and Function of CD4+ CD25+ Foxp3+ Regulatory T Cells Conveying Respiratory Tolerance," The Journal of Immunology, vol. 189, No. 4, pp. 1975-1982, 2012.
Zheng, Jian et al., "ICOS Regulates the Generation and Function of Human CD4+ Treg in a CTLA-4 Dependent Manner," PLOS One, vol. 8, No. 12, e82203, pp. 1-11, Dec. 2013.
Hedl, Matija et al., "Pattern Recognition Receptor Signaling in Human Dendritic Cells is Enhanced by ICOS Ligand and Modulated by the Crohn's Disease ICOSLG Risk Allele," Immunity, vol. 40, No. 5, pp. 734-746, May 15, 2014.
Song, S. U. et al., "Variations of Clonal Marrow Stem Cell Lines Established from Human Bone Marrow in Surface Epitopes, Differentiation Potential, Gene Expression, and Cytokine Secretion," Stem Cells and Development, vol. 17, No. 3, Jun. 24, 2008. Abstract.

* cited by examiner

Primary Examiner — Kara D Johnson
(74) Attorney, Agent, or Firm — Sughrue Mion, PLLC

(57) ABSTRACT

The present invention relates to a composition and a method for inducing CD4+ T cells to differentiate into regulatory T cells and proliferate through an induced T cell co-stimulator ligand (ICOSL) or an ICOSL-overexpressing mesenchymal stem cell and for preventing or treating regulatory T cell-mediated diseases. The induced T cell co-stimulator ligand (ICOSL) or ICOSL-overexpressing mesenchymal stem cell according to the present invention effectively suppresses the proliferation of PBMCs, induces the expression of an ICOS in regulatory T cells, thereby inducing the differentiation and proliferation of the regulatory T cells through a PI3K-Akt mechanism, and thus can effectively prevent, treat, or enhance regulatory T cell-mediated diseases.

11 Claims, 21 Drawing Sheets

Specification includes a Sequence Listing.

FIG. 17A
FIG. 17B
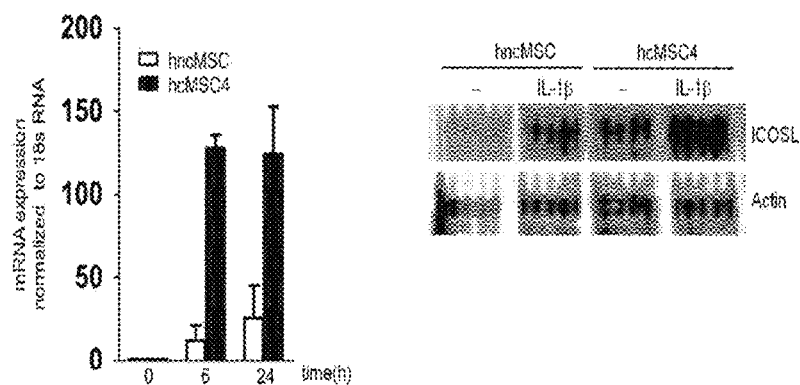
FIG. 17C
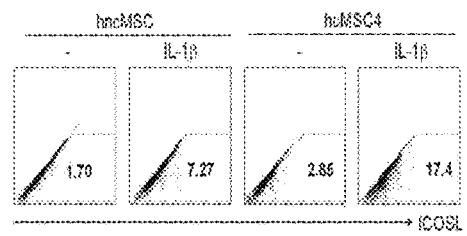

PHARMACEUTICAL COMPOSITION FOR PREVENTING OR TREATING REGULATORY T CELL-MEDIATED DISEASES

TECHNICAL FIELD

The present invention relates to a composition and a method for inducing the differentiation of CD4$^+$ T cells into regulatory T cells by induced T cell co-stimulator ligands (ICOSL) or ICOSL-overexpressing mesenchymal stem cells to prevent or treat regulatory T cell-mediated diseases.

BACKGROUND ART

One of the most critical characteristics of all normal individuals is that they do not react harmfully to the antigenic substances that constitute the self, while they have the ability to recognize, react and eliminate many non-self-antigens. An organism's non-response to self-antigens is called immunologic unresponsiveness or tolerance. Self-tolerance occurs by eliminating lymphocytes that may have specific receptors for self-antigens or by inactivating the self-reactive function after exposure to self-antigens. When it is difficult to induce or maintain self-tolerance, an immune response to self-antigen occurs, and the resulting disease is called an autoimmune disease. An example of autoimmune diseases includes an allergic disease, which refers to a disorder in which the immune system is abnormal, and substances harmless to ordinary people cause various symptoms of hypersensitivity only to a specific person. The substances causing allergic diseases are called allergens or antigens. Allergies can be caused by pollen, antibiotics, drugs, dust, food, cold air or sunlight. Symptoms of the allergic disease include urticaria, sneezing, itching, runny nose, cough, hay fever, redness, eczema, rash, and the like. Typical allergic diseases include allergic asthma with symptoms such as respiratory stenosis, increased lung mucous secretion, dyspnea and cough. In addition, there are atopic dermatitis, conjunctivitis, rhinitis and ulcerative colitis.

Studies on the importance of regulatory T cells have been actively conducted in relation to diseases caused by abnormalities of various autoimmune systems. In the early 1970s, Gershon has first introduced the concept of inhibitory T cells as the presence possibility of T cells which are capable of controlling and inhibiting the effector function of conventional T cells (R. K. Gershon and K. Kondo, Immunology, 1970, 18: 723-37). Then, studies have been conducted to elucidate the biological properties and function of regulatory T cells in many areas of immunology. In particular, it was reported by Sakaguchi in 1995 that CD25 can act as an important phenotypic marker of naturally occurring CD4$^+$ regulatory T cells (S. Sakaguchi et al., J. Immunol., 1995, 155: 1151-1164). Then, studies have been conducted to focus on the role and importance of regulatory T cells in the induction of peripheral tolerance to self-antigens.

In recent years, T cell-mediated diseases have been recognized as diseases representing multiple immune system diseases. In particular, T cells are considered to cause and sustain autoimmune diseases. Continuous activation or regular activation of self-reactive T cells results in immune responses to self-antigens. Self-reactive T cells are attracting attention as a cause of characteristic tissue injury and tissue destruction which are directly or indirectly recognized in autoimmune diseases.

Accordingly, many therapeutic agents have been proposed for autoimmune diseases and other T-cell mediated diseases. However, other therapeutic agents are still needed. In particular, its precise mechanism is required to be used as a therapeutic agent.

Meanwhile, it has been known that mesenchymal stem cells have immunoregulatory ability to regulate the activation and differentiation of immune cells in addition to multipotential. It has been known that they regulate T cells, B cells, macrophages, natural killer cells, dendritic cells, etc. in various inflammatory environments and induce regulatory T cells to inhibit immune responses. However, little is known about the specific regulator or action mechanism in the induction of regulatory T cells. Therefore, studies on specific mechanisms and effective ingredients have been required for the treatment of immune diseases such as autoimmune diseases.

DISCLOSURE

Technical Problem

The present inventors have studied mesenchymal stem cells and regulatory T cell-mediated diseases. They have identified that the induced T cell co-stimulator ligand (ICOSL) on the mesenchymal stem cell surface can induce CD4$^+$ T cell differentiation into regulatory T cells to generate many regulatory T cells and to cure T cell-mediated diseases effectively, thereby completing the present invention.

Accordingly, the object of the present invention is to provide a pharmaceutical composition for preventing or treating regulatory T cell-mediated diseases, which includes induced T cell co-stimulator ligands (ICOSL) or ICOSL-overexpressing mesenchymal stem cells and a composition and a method for inducing differentiation into regulatory T cells.

Technical Solution

In order to achieve the objects as described above, the present invention provides a pharmaceutical composition for preventing or treating a regulatory T cell-mediated disease, which includes an induced T cell co-stimulator ligand (ICOSL) or an ICOSL-overexpressing mesenchymal stem cell.

Further, the present invention provides a composition for inducing differentiation and proliferation of a CD4$^+$ T cell into a regulatory T cell, which includes an induced T cell co-stimulator ligand (ICOSL) or an ICOSL-overexpressing mesenchymal stem cell.

Further, the present invention provides a method for inducing differentiation and proliferation of a CD4$^+$ T cell into a regulatory T cell, which includes treating a CD4$^+$ T cell in vitro with an induced T cell co-stimulator ligand (ICOSL) or an ICOSL-overexpressing mesenchymal stem cell.

Advantageous Effects

In the present invention, the induced T cell co-stimulator ligand (ICOSL) or the ICOSL-overexpressing mesenchymal stem cell induces the expression of ICOS in regulatory T cells, thereby inducing the differentiation of regulatory T cells through the PI3K-Akt mechanism as well as effectively inhibiting the proliferation of PBMC so that it is possible to prevent, treat or ameliorate the T cell-mediated diseases effectively.

DESCRIPTION OF DRAWINGS

FIGS. 17A-17C illustrate the results of confirming ICOSL inducing effects of clonal (hcMSC) and non-clonal MSC (hncMSC) by IL-1β treatment through qRT-PCR (A), Western blotting (B) and flow cytometry (C).

BEST MODE

Figure 1:
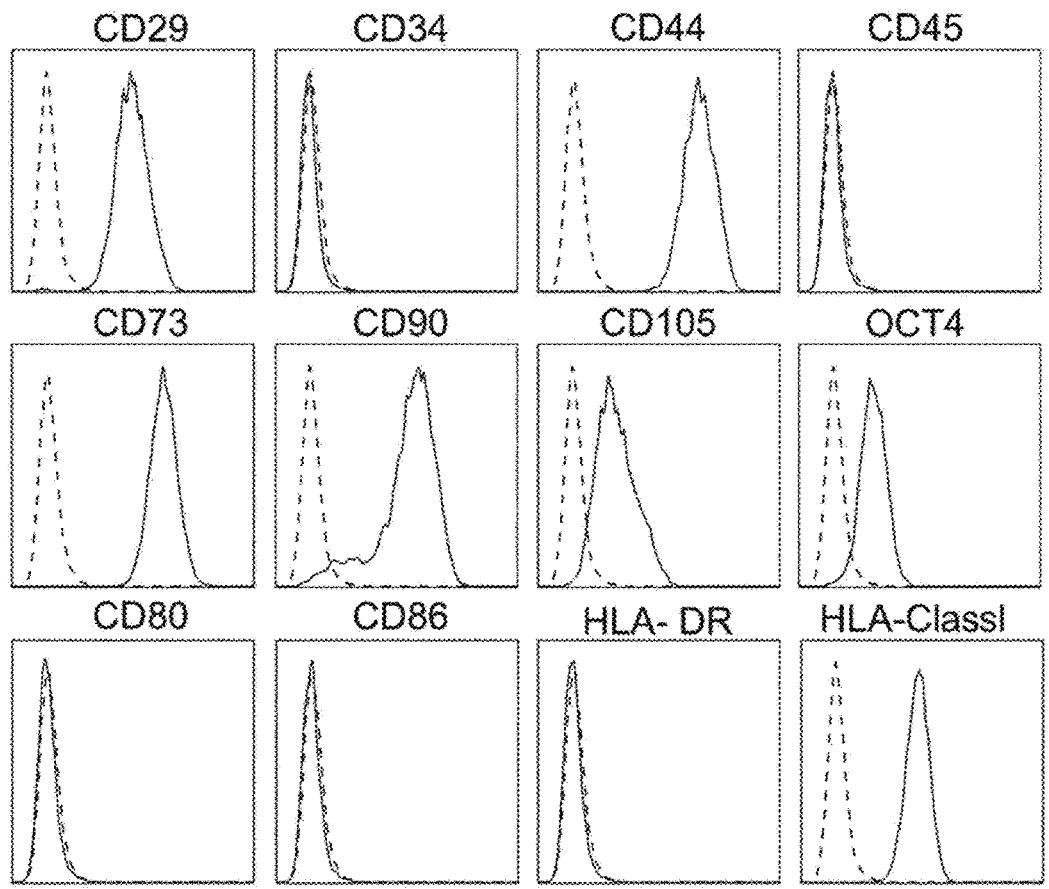
FIG. 1 illustrates the results of flow cytometry analysis on marker expression of hcMSCs in which the dotted line indicates staining with homologous control Ab, and the solid line represents the specific expression of each marker.

The present invention provides a pharmaceutical composition for the preventing or treating regulatory T cell-mediated diseases, which includes an induced T cell co-stimulator ligand (ICOSL) or an ICOSL-overexpressing mesenchymal stem cell.

The present invention has confirmed that induced T cell co-stimulator ligands (ICOSL) or ICOSL-overexpressing mesenchymal stem cells can promote the differentiation of CD4$^+$ T cells into regulatory T cells and proliferation of regulatory T cells, thereby inhibiting inflammatory or autoimmune response so that they can be used for the prevention or treatment of regulatory T cell-mediated diseases.

The term "ICOS" used herein is called H4 or AILIM, which is a superfamily of CD28, co-stimulatory molecules, and its expression is known to increase in activated T cells. ICOS can bind to ICOSL, known as B7-H2, B7RP-1, B7h, GL50, and LICOS, to mediate intercellular signaling. ICOSL is a co-stimulatory protein that carries a T cell activation signal and is encoded by the ICOSLG gene (Gene ID: 23308) in humans. ICOSL is also known to be abundantly expressed in B lymphocytes. In particular, the expression of ICOSL may increase on the surface of mesenchymal stem cells under inflammatory conditions.

In the present invention, the ICOSL may be derived from a mesenchymal stem cell. The term "derived from mesenchymal stem cells" refers to an ICOSL expressed on the surface of mesenchymal stem cells or a type isolated therefrom. Therefore, ICOSL of the present invention can include all types expressed on the surface of mesenchymal stem cells or isolated types synthesized by recombining them without limitation.

The term "ICOSL-overexpressing mesenchymal stem cells" used herein refers to stem cells in which expression on ICOSL mesenchymal stem cell surface increases compared to the normal control group. The increase in expression on ICOSL surface can be achieved, without limitation, by a method for increasing gene or protein expression known in the art, for example, the introduction of ICOSL gene and the induction of expression increase. In one embodiment of the present invention, lentivirus expressing the full-length human ICOSL gene is transduced into human clonal MSC (hcMSC) together with viral packaging constructs to induce an increase in ICOSL expression in mesenchymal stem cells, thereby producing ICOSL-overexpressing mesenchymal stem cells. ICOSL-overexpressing mesenchymal stem cells are excellent in their ability to promote the differentiation of CD4$^+$ T cells into regulatory T cells (Tregs) and the proliferation of regulatory T cells and can effectively inhibit inflammatory or autoimmune responses such as colitis.

In the present invention, the stem cells are preferably clonal mesenchymal stem cells (clonal MSCs). In the present invention, example 11 confirms that the clonal mesenchymal stem cells can be used to induce ICOSL expression which is significantly superior to human non-clonal MSC (hncMSC). Monoclonal stem cells can be obtained through the methods known in the art. However, they are preferably isolated by subfractionation culturing method disclosed in Song S U, et al. (2008) (Variations of clonal marrow stem cell lines established from the human bone marrow in surface epitopes, differentiation potential, gene expression, and cytokine secretion. Stem cells and development 17(3): 451-461.) The document is incorporated by reference into the present invention. Monoclonal stem cells have higher ICOSL expression compared with hncMSC. They also have excellent induction effect of regulatory T cell differentiation compared with hncMSC. Thus, they can be more effectively used for the treatment of inflammatory or autoimmune diseases.

In the present invention, the mesenchymal stem cells may be mesenchymal stem cells derived from one or more selected from the group consisting of umbilical cord, umbilical cord blood, bone marrow, fat, muscle, nerve, skin, amnion and placenta. Particularly, they may preferably be mesenchymal stem cells derived from bone marrow. The mesenchymal stem cells of the present invention can be understood to include not only stem cells themselves but also cultures thereof without limitation.

ICOSL of the present invention is expressed on the surface of mesenchymal stem cells and can be characterized by increasing the expression of induced T cell co-stimulator (ICOS) of T cells. ICOS is expressed on the surface of T cells during T cell activation. The present invention has confirmed that CD25$^+$FoxP3$^+$ Tregs showed higher ICOS expression through co-culturing hcMSC and CD4$^+$ T cells.

Further, ICOSL of the present invention can be characterized by activating the PI3K-Akt signaling pathway. ICOSL binds to ICOS of T cells, thereby promoting Akt phosphorylation in Treg and activating PI3K-Akt signaling pathway.

Another aspect of the present invention provides a pharmaceutical composition for preventing or treating regulatory T cell-mediated diseases, in which ICOSL-overexpressing mesenchymal stem cells are treated with one or more selected from the group consisting of IL-1β, TNF-α, IL-6, IL-2, IL-1, and LPS (lipopolysaccharide).

Mesenchymal stem cells may be treated with one or more selected from the group consisting of IL-1β, TNF-α, IL-6, IL-2, IL-1, and LPS (lipopolysaccharide), preferably IL-1β, TNF-α and LPS, most preferably IL-1β, thereby playing a role in priming stem cells. More specifically, mesenchymal stem cells are treated with one or more selected from the group consisting of IL-1β, TNF-α and LPS (lipopolysaccharide) to induce an increase in the expression of ICOSL in the mesenchymal stem cells. Therefore, it is possible to strongly promote the differentiation and proliferation of regulatory T cells (Tregs) by producing ICOSL overexpressing mesenchymal stem cells. Further, the produced ICOSL-overexpressing mesenchymal stem cells can be used as a stem cell therapeutic agent for preventing or treating regulatory T cell-mediated diseases through promoting effects of regulatory T cell differentiation and proliferation.

Thus, the present invention may be provided in a type of a kit including mesenchymal stem cells and one or more selected from the group consisting of IL-1β, TNF-α, IL-6, IL-2, IL-1 and LPS (lipopolysaccharide), preferably one or more selected from the group consisting of IL-1β, TNF-α, and LPS, most preferably IL-1β positioned in individual sections. Mesenchymal stem cells are pre-treated with one or more selected from the group consisting of IL-1β, TNF-α, and LPS (lipopolysaccharide), most preferably IL-1β to induce ICOSL-overexpression in mesenchymal stem cells, thereby preparing a composition for preventing or treating a regulatory T cell-mediated disease, which includes ICOSL-overexpressing mesenchymal stem cells.

The term "regulatory T cell-mediated disease" used herein refers to a disease which is caused by an abnormality or deficiency of regulatory T cells, and specifically, it may be an inflammatory disease or an autoimmune disease.

In one aspect of the present invention, the inflammatory disease may include one or more selected from the group consisting of lupus, Sjogren's syndrome, rheumatoid arthritis, fibromyositis, scleroderma, ankylosing spondylitis, Behcet's disease, aphthous stomatitis, Guillian Barre syndrome, alopecia areata, dermatomyositis, Crohn's disease, colitis, polyarteritis *nodosa*, relapsing polychondritis, and autoimmune thrombocytopenia.

Further, in one aspect of the present invention, the autoimmune disease may include one or more selected from the group consisting of rheumatoid arthritis, systemic scleroderma, insulin-dependent childhood diabetes mellitus due to pancreatic cell, areata alopecia, psoriasis, pemphigus, asthma, aphthous stomatitis, chronic thyroiditis, partial acquired aplastic anemia, primary hepatocirrhosis, ulcerative colitis, Behcet's disease, Crohn's disease, silicosis, asbestosis, IgA kidney disease, poststreptococcal glomerulonephritis, Sjogren's syndrome, Guillain Barre syndrome, dermatomyositis, polymyositis, multiple sclerosis, autoimmune hemolytic anemia, autoimmune encephalomyelitis, myasthenia gravis, Grave's thyroid hyperplasia, nodular polyarteritis, ankylosing spondylitis, fibrositis, temporal arteritis, Wilson's disease, Pakoni's syndrome, multiple myeloma, and systemic lupus erythematosus.

The composition of the present invention may include a pharmaceutically acceptable carrier and/or an additive and the like. For example, it may include sterile water, normal saline, a conventional buffer (e.g., phosphoric acid, citric acid, and other organic acid), a stabilizer, salt, an antioxidant, a surfactant, a suspending agent, an isotonic agent or a preservative. Further, it may, but not be limited thereto, include an organic substance such as a biopolymer and an inorganic substance such as hydroxyapatite, specifically, a collagen matrix, a polylactic acid polymer or its copolymer, a polyethylene glycol polymer or its copolymer, a chemical derivative thereof, and a mixture thereof. Examples of the stabilizer may include dextran 40, methylcellulose, gelatin, sodium sulfite, sodium metasulfate, and the like. Examples of the antioxidant may include a chelating agent such as erythorbic acid, dibutylhydroxytoluene, butylhydroxyanisole, α-tocopherol, tocopheryl acetate, L-ascorbic acid and its salt, L-ascorbic acid palmitate, L-ascorbic acid stearate, sodium hydrogen sulfite, sodium sulfite, gallic acid triamyl, gallic acid propyl or ethylenediaminetetraacetic acid sodium (EDTA), sodium pyrophosphate, and sodium metaphosphate. Examples of the suspending agent may include methylcellulose, polysorbate 80, hydroxyethylcellulose, gum arabic, tragacanth gum, sodium carboxymethyl cellulose, and polyoxyethylene sorbitan monolaurate. Examples of the isotonic agent may include D-mannitol and sorbitol. Examples of the preservative may include methylparaben, ethylparaben, sorbic acid, phenol, cresol, and chloro-cresol.

The pharmaceutical preparation including ICOSL-overexpressing mesenchymal stem cells, cultures thereof, or ICOSL according to the present invention thus prepared can be administered with other stem cells used for transplantation and other uses or in the form of a mixture with such stem cells using administration method conventionally used in the art. In detail, it may, but not be limited thereto, be administered by direct engraft or transplant to a diseased site of a patient in need of treatment or by direct transplant or injection to an abdominal cavity. Further, the administration may be performed by non-surgical administration using a catheter and surgical administration such as injection or transplantation after the incision of a disease site. However, the non-surgical administration method using a catheter is more appropriate. Further, it may be performed by parenteral injection according to a conventional method, for example, direct injection into a lesion, as well as implantation by intravascular injection. The single dose of the stem cells is $1.0 \times 10^4$ to $1.0 \times 10^{10}$ cells/kg by body weight, specifically $1.0 \times 10^5$ to $1.0 \times 10^9$ cells/kg by body weight, more specifically $1.0 \times 10^6$ to $1.0 \times 10^8$ cells/kg by body weight, and it may be administered once or several times in divided doses. However, it should be understood that the actual dose of the active ingredient is determined depending on various relevant factors such as a disease to be treated, the severity of a disease, the route of administration and the weight, age and sex of a patient. The dose is not intended to limit the scope of the present invention in any way.

Further, the present invention provides a method for preventing or treating a regulatory T cell-mediated disease, which includes administering an induced T cell co-stimulator ligand (ICOSL) or an ICOSL-overexpressing mesenchymal stem cell to an individual.

Preferably, the individual is a mammal including a human, which is a patient in need of regulatory T cell-mediated disease therapy, including a regulatory T cell-mediated disease patient under treatment, a regulatory T cell-mediated disease patient who has been treated and a regulatory T cell-mediated disease patient in need of treatment. It may also include a patient who underwent surgical surgery for the treatment of regulatory T cell-mediated disease.

Further, the present invention may use and treat induced T cell co-stimulator ligands (ICOSL) or ICOSL-overexpressing mesenchymal stem cells in combination with drugs or treatments for other conventional regulatory T cell-mediated disease therapies. When the induced T cell co-stimulator ligands (ICOSL) or ICOSL-overexpressing mesenchymal stem cells of the present invention are used in combination, it can be treated simultaneously or sequentially with other drugs or treatments for regulatory T cell-mediated disease therapies.

Further, one aspect of the present invention provides a composition for inducing differentiation and proliferation of a $CD4^+$ T cell into a regulatory T cell, which includes an induced T cell co-stimulator ligand (ICOSL) or an ICOSL-overexpressing mesenchymal stem cell.

The term "induction of differentiation and proliferation" refers to the promotion of differentiation of $CD4^+$ T cells into regulatory T cells by direct contact between $CD4^+$ T cells and ICOSL on the surface of the mesenchymal stem cell and proliferation of regulatory T cells which are differentiated and induced by induced T cell co-stimulator ligands (ICOSL) or ICOSL-overexpressing mesenchymal stem cells.

In order to further promote expression of ICOSL on mesenchymal stem cells, the composition may further include one or more selected from the group consisting of IL-1β, TNF-α, IL-6, IL-2, IL-1 and LPS (lipopolysaccharide), preferably, one or more selected from the group consisting of IL-1β, TNF-α and LPS, and most preferably, IL-1β. The one or more kinds selected from the group consisting of IL-1β, TNF-α and LPS are substances which prime mesenchymal stem cells, thereby promoting ICOSL overexpression on the surface of mesenchymal stem cells.

In another aspect of the present invention, the present invention provides a method for inducing differentiation and proliferation of a $CD4^+$ T cell into a regulatory T cell, which includes treating a $CD4^+$ T cell in vitro with an induced T cell co-stimulator ligand (ICOSL) or an ICOSL-overexpressing mesenchymal stem cell.

In the method, the ICOSL-overexpressing mesenchymal stem cell may be pre-treated with one or more selected from the group consisting of IL-1β, TNF-α, IL-6, IL-2, IL-1 and LPS (lipopolysaccharide), preferably one or more selected from the group consisting of IL-1β, TNF-α and LPS, and most preferably IL-1β. ICOSL or stem cells with increased ICOSL expression may induce increased expression of ICOS in $CD4^+$ T cells by direct contact with $CD4^+$ T cells and may promote differentiation into regulatory T cells and proliferation of the differentiated regulatory T cells.

In this method, the treatment may include both culturing $CD4^+$ T cells in a well coated with ICOSL or co-culturing $CD4^+$ T cells with ICOSL-overexpressing mesenchymal stem cells.

It should be construed that the numerical values described herein include equivalent ranges unless otherwise indicated.

Hereinafter, preferable examples of production examples, examples and preparation examples are described to facilitate understanding of the present invention. However, the following production examples, examples and preparation examples are provided only for the easier understanding of the present invention but do not limit the contents of the present invention.

[Modes of the Invention]

EXAMPLE 1

Analysis of Characterization of Human Clonal MSC (hcMSC)

Human bone marrow was collected from a healthy male donor. The experiment was performed according to approval by the Institutional Review Board of Inha University Hospital (IRB #10-51). The hcMSCs were isolated by the subfractionation culturing method according to the prior document (Song S U, et al. (2008), Variations of clonal marrow stem cell lines established from the human bone marrow in surface epitopes, differentiation potential, gene expression, and cytokine secretion. Stem cells and development 17(3):451-461.). All hcMSCs were incubated in Dulbecco's modified Eagle's medium (DMEM) with low glucose supplemented with 10% fetal bovine serum (FBS) and 1% penicillin/streptomycin. The isolated hcMSCs were analyzed by flow cytometry to identify various cell surface markers. The antibodies used for the analysis are as follows: anti-CD29 (Serotec, Kidlington, UK), anti-CD44 (Serotec), anti-CD105 (Serotec), anti-CD34 (BD Biosciences, San Diego, Calif., USA), anti-CD45 (BD Biosciences), anti-CD90 (BD Biosciences), anti-CD73 (BD Biosciences), anti-HLA class I (BD Biosciences), anti-HLA DR (BD Biosciences), anti-CD80 (eBiosciences, San Diego, Calif., USA), anti-CD86 (SouthernBiotech, Birmingham, Ala., USA), and anti-Oct4 (Cell Signaling Technology, Danvers, Mass., USA). The cells were analyzed using a flow cytometer (FACS Calibur; BD Biosciences). Isotype-matched control antibodies were used as controls. The results of identifying expression of surface markers of hcMSCs using flow cytometry are illustrated in FIG. 1.

As illustrated in FIG. 1, the expression was found to be positive for CD29, CD44, C73, CD90, CD105, Oct-4 and HLA class I but was found to be negative for CD34, CD45 and HLA-DR. The expression was also found to be negative for co-stimulatory factors CD80 and CD86.

In vitro PBMC activity of hcMSCs was determined by CFSE assay. hcMSCs were co-cultured with PBMCs treated with PHA. More specifically, $1 \times 10^6$ PBMCs were stained with 1 µM CFSE, the stained PBMCs were stimulated with 1 µg/mL PHA in the presence or absence of $1 \times 10^5$ or $1 \times 10^6$ hcMSCs. After PHA stimulation for 72 hours, PBMCs were harvested and analyzed by flow cytometry. The results are illustrated in FIG. 2.

Figure 2:
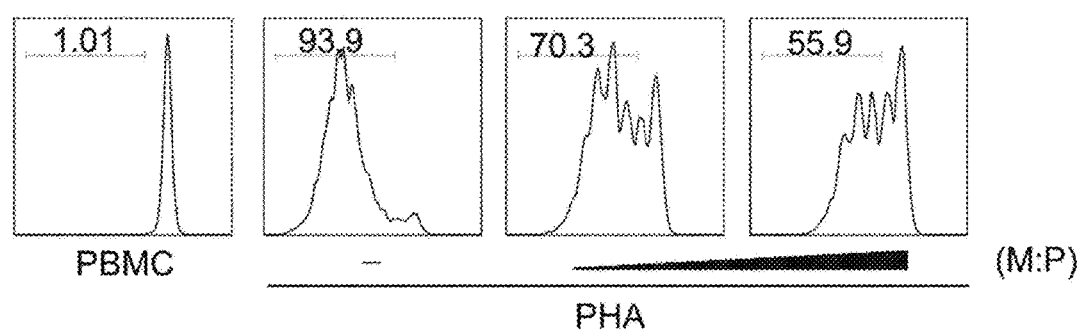
FIG. 2 illustrates the results of CFSE assay on in vitro T cells suppressive activity of hcMSCs (M: hcMSC and P: CFSE-stained PBMC).

As illustrated in FIG. 2, when hcMSCs were co-cultured with activated PBMCs treated with PHA, they inhibited proliferation of PBMCs.

EXAMPLE 2

Identification of Induction of Tregs Differentiation by hcMSC

Peripheral blood mononuclear cells (PBMCs) were collected from healthy donors and separated by ficoll-hypaque density gradient centrifugation. CD4$^+$ T cells from PBMC were obtained using CD4$^+$ T cell Isolation Kit MicroBeads (Miltenyi Biotech, Bisley, Surrey, UK).

In order to identify the Treg differentiation, isolated CD4$^+$ T cells were incubated in a complete medium containing RPMI 1640 supplemented with 10% FBS, 2 mM L-glutamine and 100 U/mL penicillin. In a 24-well plate, the wells were coated with 1 µg/mL anti-CD3 monoclonal antibody at 4° C. overnight. Further, purified CD4$^+$ T cells were stimulated by anti-CD3, anti-CD28, IL-2, TGF-b1 and atRA, which was a condition for Treg differentiation. In order to identify Treg differentiation, FoxP3 and CD25 expression was confirmed at day 2 and day 5.

In order to confirm the relationship between Treg induction and hcMSC, CD4$^+$ T cells were co-cultured with hcMSCs or only CD4$^+$ T cells were incubated without hcMSCs. The results were confirmed by FoxP3 and CD25 expression analysis and the increase of FoxP3$^+$CD4$^+$CD25$^+$ cells at day 1 to day 3. The results are illustrated in FIG. 3.

Figure 3A:
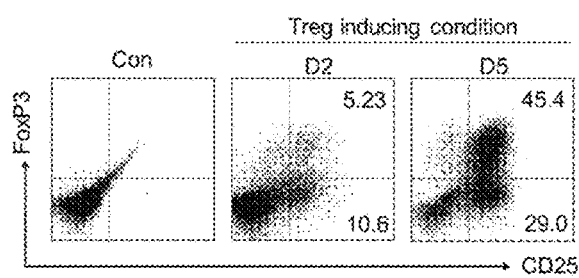
FIGS. 3A-3C illustrate the results of flow cytometry analysis of Treg differentiation of CD4+ T cells under Treg inducing condition at day 2 and day 5 (A), the results of confirming the effect of hcMSCs by expression of FoxP3 and CD25 (B), and the results of confirming the effect of hcMSCs by increases of FoxP3$^+$CD4$^+$CD25$^+$ cells (C) (*, P=0.017).
Figure 3B:
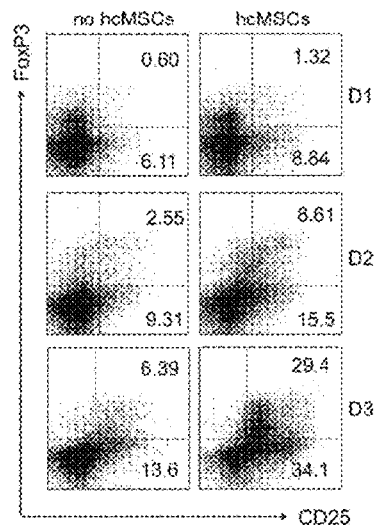
Figure 3C:
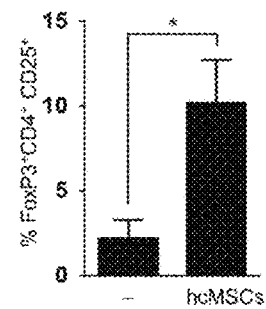

As illustrated in FIG. 3, FoxP3$^+$CD25$^+$ Tregs were found progressively under Treg inducing condition (A). Further, co-culture with hcMSCs significantly induced more FoxP3$^+$CD25$^+$ Tregs (B) and also increased the population of FoxP3+CD25$^+$ derived from CD4$^+$ T cells (C). The results suggest that hcMSCs can induce Treg strongly.

EXAMPLE 3

Identification of Contact-Dependent Induction Effect of hcMSC hcMSCs were co-cultured with CD4$^+$ T cells, and the appearance of these cells was confirmed by a light microscope (×400). The cells were classified into adherent or floating type depending on the presence types. Their CD25 and FoxP3 expression levels were compared by flow cytometry.

Figure 4A:
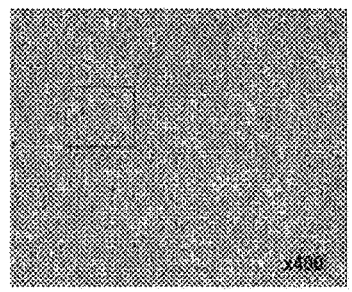
FIGS. 4A-4B illustrate the results of confirming the shape of CD4$^+$ T cells obtained by co-culturing hcMSCs with CD4$^+$ T cells through a microscope (A) and the results of comparing changes of CD25$^+$ and FoxP3$^+$ in floating CD4$^+$ T cells and adherent CD4$^+$ T cells (B) (Blue box: floating CD4$^+$ T cells and red box: hcMSC-adherent CD4$^+$ T cells).
Figure 4B:
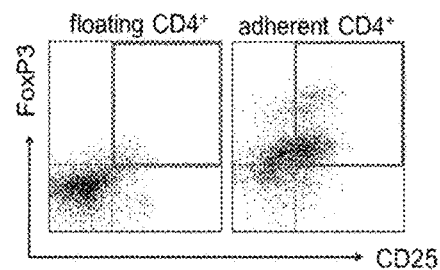

As illustrated in FIG. 4, it was confirmed by a light microscope that CD4$^+$ T cells were present in an adherent or floating type (A). Some CD4$^+$ T cells were in contact with hcMSCs and the adherent CD4$^+$ T cells highly expressed CD25 and FoxP3. However, some CD4$^+$ T cells were floating in the culture medium. These floating cells expressed a lower level of CD25 and FoxP3 than adherent cells did (B).

To further confirm the requirement of cell contacts in MSC-mediated Treg induction, transwell assay was performed for 2 days. For transwell assay, CD4$^+$ T cells were incubated in the lower chamber and hcMSCs were in the upper chamber. It was confirmed whether or not the Treg induction effect by hcMSCs could be obtained by this culture method, and the results are illustrated in FIG. 5.

Figure 5:
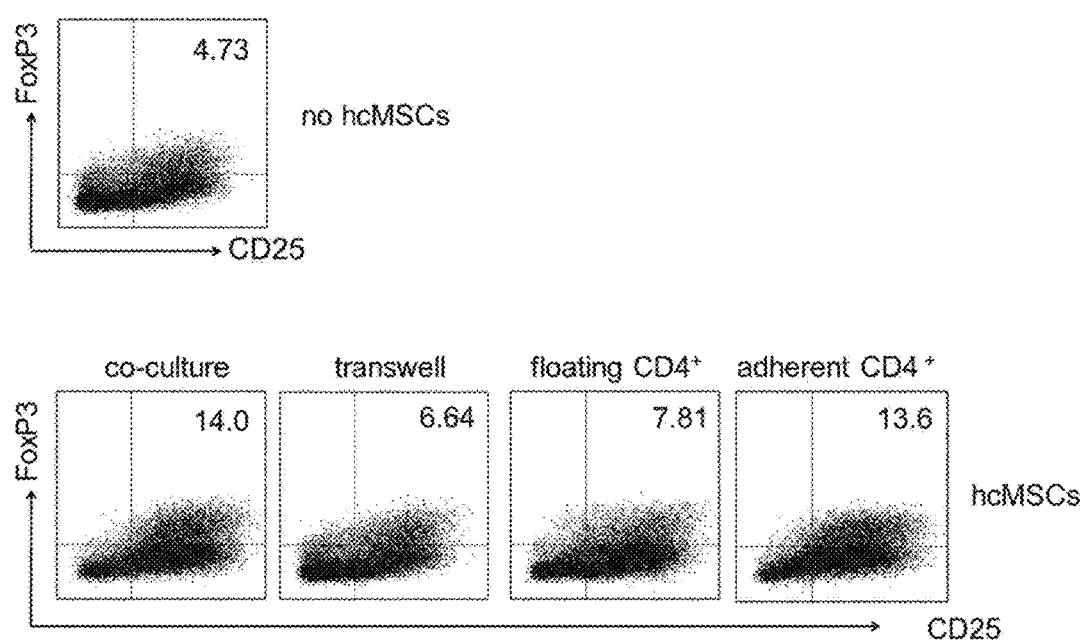
FIG. 5 illustrates the results of comparing changes in CD25$^+$ and FoxP3$^+$ in floating CD4$^+$ T cells, adherent CD4$^+$ T cells, co-culturing hcMSCs and trans-well culturing.

As illustrated in FIG. 5, when CD4$^+$ T cells and hcMSCs were separately incubated by transwell assay, hcMSCs did not affect the expression of CD25 and FoxP3 in CD4$^+$ T cells.

These results indicate that hcMSC-mediated Treg induction requires cell-cell contacts, suggesting that direct interaction between hcMSCs and T cells may play a critical role in transducing induction signals for Treg differentiation in CD4$^+$ T cells.

EXAMPLE 4

Identification of Relationship Between ICOSL Expression on hcMSC and Treg Induction It was confirmed that the direct interaction between hcMSC and T cells induces Treg differentiation. Therefore, it was expected that ICOSL expression on hcMSC would play an essential role in signal transduction. Thus, experiments were carried out to confirm this. hcMSC and CD4$^+$ Treg were co-cultured for 2 days under Treg induction condition. The expression of ICOSL protein on hcMSC was confirmed by flow cytometry. The expression of mRNA was confirmed by qRT-PCR after 24 hours of co-culture. Non-adherent CD4$^+$ T cells were removed, followed by immunofluorescent staining. Then, ICOSL expression on hcMSC was observed by a confocal microscope. Total RNA of hcMSC was measured using EasyBlue RNA isolation reagent (Intron, Biotechnology, Sungnam, Korea), and cDNAs were synthesized from 2 μg of total RNA using the AccuPower cDNA synthesis kit (Bioneer, Daejeon, Korea). Reverse transcription polymerase chain reaction (RT-PCR) was performed using AccuPower PCR premix (Bioneer). The amplified PCR products were electrophoresed on 1% agarose gel containing SybrSafe and analyzed by a fluorescence image analyzer. PCR was carried out using the following primers: IL-10 (forward 5'-ATCCAAGACAACAC-TACTAA-3' (SEQ ID NO:1) and reverse 5'-TAAATATCCTCAAAGTTCC-3' (SEQ ID NO:2)), IL-1 (forward 5'-GCTGAGTGCTGCAAAGTACC-3' (SEQ ID NO:3) and reverse 5'-TGAGGAGGGA-CTTGTGACTG-3' (SEQ ID NO:4)), IL-1R (forward 5'-ATT-GATGTTCGTCCCTGTCC-3' (SEQ ID NO:5) and reverse 5'-CCTCCACCTTAGCAGGAACA-3' (SEQ ID NO:6)) and GAPDH (forward 5'-CCACTGGCGTCTTCACCAC-3' (SEQ ID NO:7) and reverse 5'-CCTGCTTCAC-CACCTTCTTG-3' (SEQ ID NO:8)).

To confirm ICOSL mRNA, quantitative RT-PCR (qRT-PCR) was performed using TaqMan probes (Assay ID: Hs00323621_m1; Applied Biosystems, Foster city, Calif., USA) and TaqMan Universal PCR Master Mix (Applied Biosystems). mRNA level was normalized to 18S rRNA (Hs03928985_g1). The results are illustrated in FIG. 6.

Figure 6A:
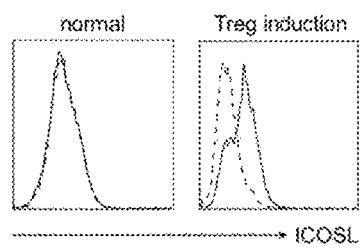
FIGS. 6A-6C illustrate the results of confirming changes in ICOSL protein expression by co-culturing hcMSCs with CD4$^+$ T cells (A), the results of confirming changes in mRNA expression thereby (B), and the results of confirming ICOSL expression by a confocal microscope (C) (magnification: ×200, ×400).
Figure 6B:
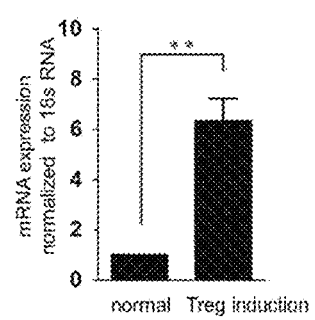
Figure 6C:
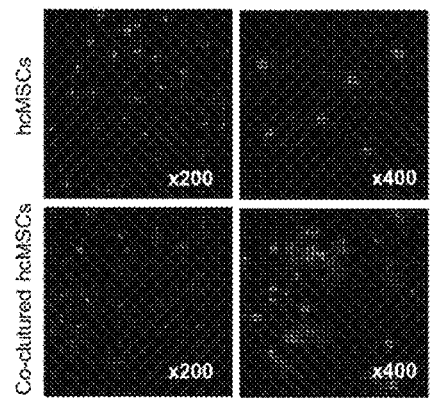

As illustrated in FIG. 6, it was confirmed, by a flow cytometry, that ICOSL was significantly up-regulated on co-cultured hcMSCs under Treg differentiation condition (A). Further, consistent with the flow cytometric result, qRT-PCR revealed that mRNA expression of ICOSL on hcMSCs increased during co-culture (B). ICOSL expression in co-cultured hcMSCs was further confirmed by immunofluorescence staining (C).

These results indicate that ICOSL expression on hcMSC increases under Treg induction condition.

EXAMPLE 5

Identification of Increased Expression of ICOS by T Cell Co-Culturing with hcMSC It was known that ICOS was up-regulated in T cells upon activation and that ICOSL expressed on APCs can inhibit T cell responses by promoting the induction of Tregs. To examine whether hcMSCs affect T cells to express ICOS, hcMSCs and CD4$^+$ T cells were co-cultured for 48 hours under Treg differentiation condition. The induction of ICOS of CD4$^+$ T cells in the presence of hcMSC was confirmed by 5 independent experiments. The results are illustrated in FIG. 7.

Figure 7A:
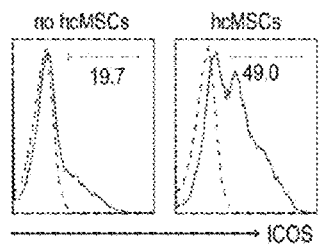
FIGS. 7A-7B illustrate the results of confirming changes in ICOS protein expression by co-culturing hcMSCs with CD4$^+$ T cells (A) and the results of confirming changes in FoxP3, CD25 and ICOS expression in CD4$^+$ cells thereby (B).
Figure 7B:
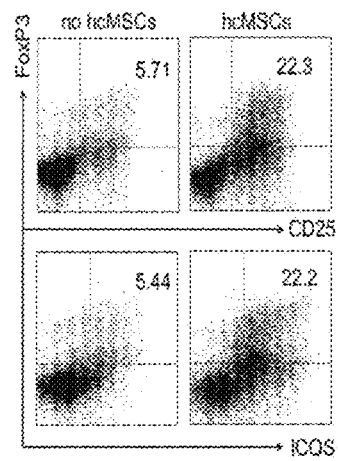

As illustrated in FIG. 7, ICOS further increased in the co-culture condition of CD4$^+$ T cells and hcMSC (A). Interestingly, CD25$^+$FoxP3$^+$ Tregs expressed higher ICOS in the presence of hcMSCs (B). These results indicate that hcMSCs drive CD4$^+$ T cells to display FoxP3$^+$ Treg phenotypes with higher expression of ICOS.

EXAMPLE 6

Identification of ICOS-ICOSL Signaling Pathway

To obtain direct evidence of the interaction between Treg induction and ICOSL on hcMSCs, the function of ICOSL was blocked, and its change was observed. To block the function of ICOSL, the neutralizing antibody treatment against ICOSL and the gene targeting experiments were carried out.

In detail, to block the function of ICOSL, 10 μg/mL anti-ICOSL neutralizing antibody was added to the co-cultures of hcMSCs and CD4$^+$ T cells. Cell surface was stained with fluorescein isothiocyanate (FITC) or allophycocyanin (APC)-conjugated CD25, APC and PE-conjugated ICOS, FITC-conjugated CD4 (eBiosciences) for 20 minutes at 4° C. in the dark. Co-culture was carried out for 2 days, and the ratio of FoxP3$^+$CD25$^+$ and Foxp3$^+$ICOS$^+$ population was determined by flow cytometry.

Meanwhile, ICOS-ICOSL interaction is important in IL-10 production, and Treg expressing ICOS promotes IL-10 production. Therefore, IL-10 production by Treg induced by hcMSCs was analyzed by a flow cytometry analyzer and ELISA. IL-10 production was confirmed after re-stimulating cells with phorbol 12-myristate 13-acetate (PMA; 40 ng/mL; Sigma) and Ionomycin (1 μg/mL; Sigma) for 5 hours. Monensin (4 μM; Sigma) was added to terminate the stimulation.

Figure 8A:
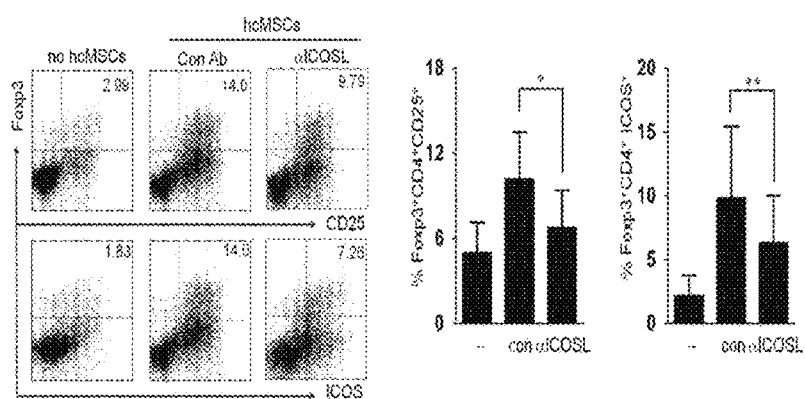
FIG. 8A illustrates the results of flow cytometry analysis of changes in FoxP3, CD25 and ICOS expression by co-culturing hcMSCs with CD4$^+$ T cells, which is treated with anti-ICOSL Ab (10 µg/mL) or control Ab, CD4$^+$ T cells and confirming FoxP3$^+$CD4$^+$CD25$^+$ T cells and FoxP3$^+$CD4$^+$ICOS$^+$ T cells (*P=0.017 and **P=0.049).
Figure 8B:
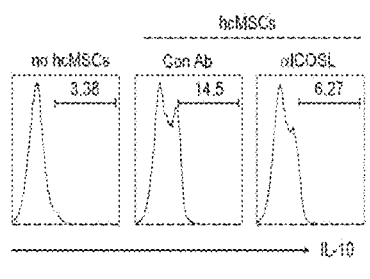
FIG. 8B illustrates the results of flow cytometry analysis of IL-10 production of CD4$^+$ T cells by co-culturing hcMSCs with CD4$^+$ T cells, which is treated with anti-ICOSL Ab (10 µg/mL) or control Ab, CD4$^+$ T cells.
Figure 8C:
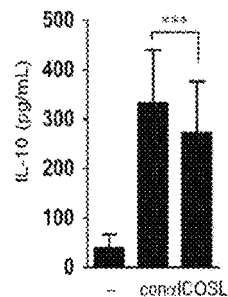
FIG. 8C illustrates the results of ELISA thereof (***P=0.03).

In the hcMSC-mediated Treg induction, the results of blocking the function of ICOSL through the neutralizing antibody treatment are illustrated in FIG. 8.

As illustrated in FIG. 8, the neutralizing antibody treatment (αICOSL) on ICOSL allowed CD25$^+$FoxP3$^+$ Treg population to be remarkably reduced, thereby decreasing the ICOS expression in the Treg population (A). Meanwhile, hcMSC significantly increased IL-10 production in Treg, whereas IL-10 production decreased with the ICOSL neutralizing antibody treatment (B and C).

Further, ICOSL was knocked down in hcMSCs by infecting lentiviruses expressing shRNA targeting ICOSL (shICOSL). Then, changes in Foxp3, ICOS and CD25 expression were observed for the Treg population. For lentiviral short-hairpin RNA (shRNA)-mediated gene knockdown, ICOSL virus particles were purchased from Santa cruz (Santa cruz biotechnology, Santa cruz, Calif., USA). For shRNA transfection, 1×10$^5$ hcMSCs were seeded onto a 24-well plate. The next day, adherent hcMSCs were infected by control (shCon) or ICOSL shRNA lentiviral particles (shICOSL) in the presence or absence of polybrene (5 μg/mL, Santa Cruz) for 24 hours. Knockdown of ICOSL was confirmed by qRT-PCR analysis. The infected hcMSCs were further co-cultured with CD4$^+$ T cells under Treg induction condition. The results of knockdown and Treg induction effects according to knockdown are illustrated in FIG. 9.

Figure 9A:
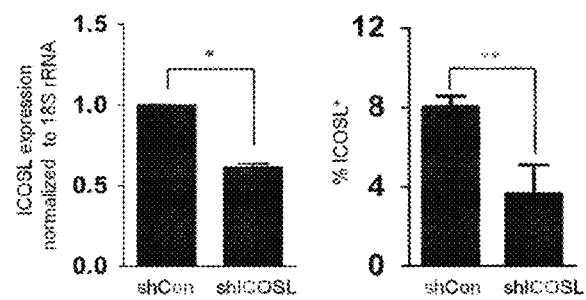
FIGS. 9A-9B illustrate the results of qRT-PCR and flow cytometry analysis of the knockdown result according to gene targeting using shRNA (shICOSL) targeting ICOSL (A) and the change of Treg induction effect according to the knockdown (B) (*P=0.008 and **P=0.013).
Figure 9B:
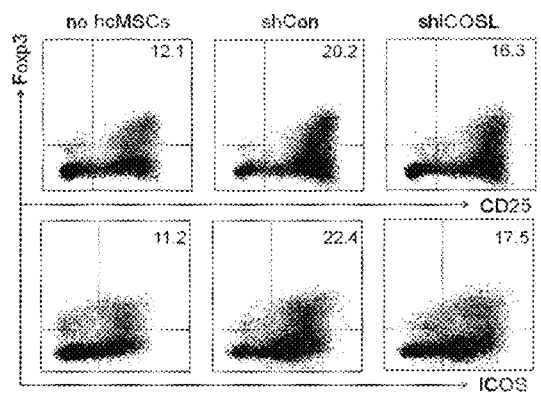

As illustrated in FIG. 9, ICOSL was effectively knocked down by shRNA treatment (A). Treg induction of hcMSCs by this knockdown was reduced in such ICOSL knockdown group (B).

These results demonstrate that ICOSL plays a critical role in hcMSC-mediated Treg induction.

EXAMPLE 7

Treg Population Induction by ICOSL Overexpression in hcMSC 7.1 Identification of ICOSL Overexpression Induction In MSC-mediated Treg induction, ICOSL over-expression in hcMSCs was induced, and its effects were investigated. For ICOSL over-expression in hcMSCs, lentivirus expressing full-length human ICOSL gene was transduced into hcMSCs along with viral packaging constructs. More specifically, full-length human ICOSL gene expression vectors were sub-cloned into C-terminal mGFP tagged pLenti vectors. For cDNA quantification, they were transformed into competent *E. coli* cells and resulting clones were sequenced for the confirmation ICOSL insertion. 293FT cells were transfected with the ICOSL expression vector using Lenti-vpak packaging kit (Origene). $2.5 \times 10^6$ of 293 FT cells for lentivirus production were seeded in a 100-mm culture dish. Two days later, the virus-containing culture supernatant was harvested and used to infect hcMSCs. After hcMSCs were infected, qRT-PCR, Western blotting and flow cytometry were used to check the level of ICOSL overexpression. The results are illustrated in FIG. 10.

Figure 10A:
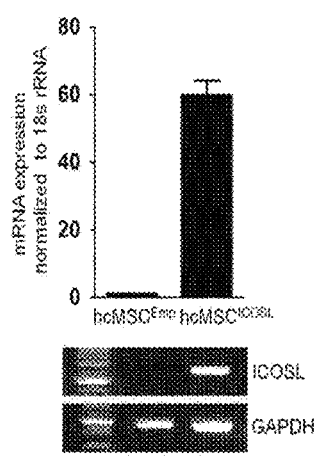
FIGS. 10A-10C illustrate the results of qRT-PCR (A), Western blotting (B), and flow cytometry analysis (C) on the increase in the expression of ICOSL in hcMSC (hcMSC$^{ICOSL}$) in which lentiviruses expressing full-length human ICOSL were transduced and the MSC control (hcMSC$^{Emp}$) in which the empty vectors were transduced.
Figure 10B:
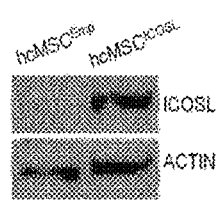
Figure 10C:
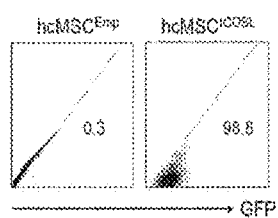

As illustrated in FIG. 10, it was confirmed that hcMSCs (hcMSC$^{ICOSL}$) transduced with lentivirus expressing full-length human ICOSL increased mRNA and protein expression of ICOSL compared with control MSC transduced with empty vector (hcMSC$^{Emp}$) (A and B). Further, ICOSL induction was further confirmed through the expression of ICOSL-fused lentiviral vector expression GFP. The results indicated that GFP increased in hcMSC$^{ICOSL}$ to ICOSL overexpression efficiently.

7.2 Identification of Increased Treg Induction in hcMSC$^{ICOSL}$

It was confirmed that ICOSL was overexpressed in hcMSC in 7.1. Thus, the flow cytometry and ELISA were used to confirm whether or not Treg induction in hcMSC$^{ICOSL}$ was increased. The results are illustrated in FIG. 11.

Figure 11A:
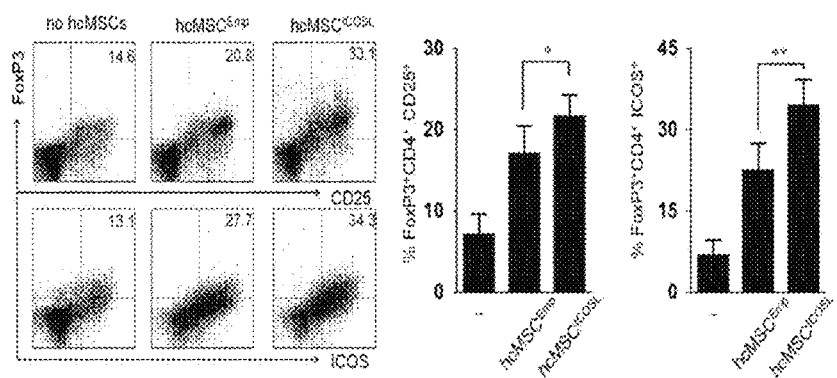
FIGS. 11A-11C illustrate the results of flow cytometry and ELISA of the effect of increasing hcMSC$^{ICOSL}$ Treg induction (A) (*P=0.045 and P=0.049) and the results of flow cytometry analysis (B) and ELISA (C) of the effect of IL-10 secretion increase by Treg (*P=0.034).
Figure 11B:
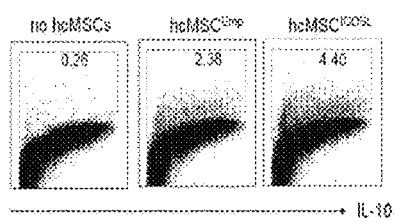
Figure 11C:
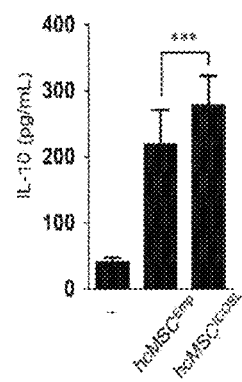

As illustrated in FIG. 11, hcMSC$^{ICOSL}$ induced more CD25$^+$FoxP3$^+$ Tregs as compared to the control in which the empty vector was introduced, and Tregs induced by hcMSC$^{ICOSL}$ expressed higher expression of ICOS (A). Further, the flow cytometry and ELISA analysis were used to confirm that Treg induced by hcMSC$^{ICOSL}$ further promoted production and secretion of IL-10, an effector anti-inflammatory cytokine. These results indicate that ICOSL plays a critical role in MSC-mediated Treg induction, which is a result of showing that ICOSL of MSC plays a role as an effective Treg inducer.

EXAMPLE 8

Identification of PBMC Proliferation Inhibitory Effect of hcMSC-Induced Treg

It was confirmed that hcMSCs induced so that CD4$^+$ T cells exhibited Treg phenotypes expressing CD25, FoxP3, ICOS and IL-10 under Treg induction condition. Meanwhile, Treg was known to have a lymphocyte inhibitory activity both in vitro and in vivo. Thus, it was confirmed whether Treg suppressed proliferation of activated lymphocytes.

CD4$^+$ T cells purified from PBMCs cells were co-cultured with hcMSC$^{ICOSL}$ or hcMSC$^{Emp}$ under Treg-inducing condition for 2 days. Then, CD25$^+$ cells were isolated from CD4$^+$ T cells containing Treg population. PBMCs were labeled with 10 μM CFSE in pre-warmed PBS at a final concentration of $10^7$ cells/mL. PBMCs labeled with CFSE were stimulated with 1 μg/mL anti-CD3 mAb (eBiosciences) and 3 μg/mL anti-CD28 mAb (eBiosciences) for 3 days. CD25$^+$ population isolated from co-cultures of CD4$^+$ T cells and hcMSC$^{ICOSL}$ or hcMSC$^{Emp}$ was co-cultured with CFSE-labeled and activated PBMCs at a ratio of 1:5 or 1:10 (Tregs:PBMCs) for 3 days. PBMC proliferation was analyzed by flow cytometer assessing the CFSE dilution. The results are illustrated in FIG. 12.

Figure 12:
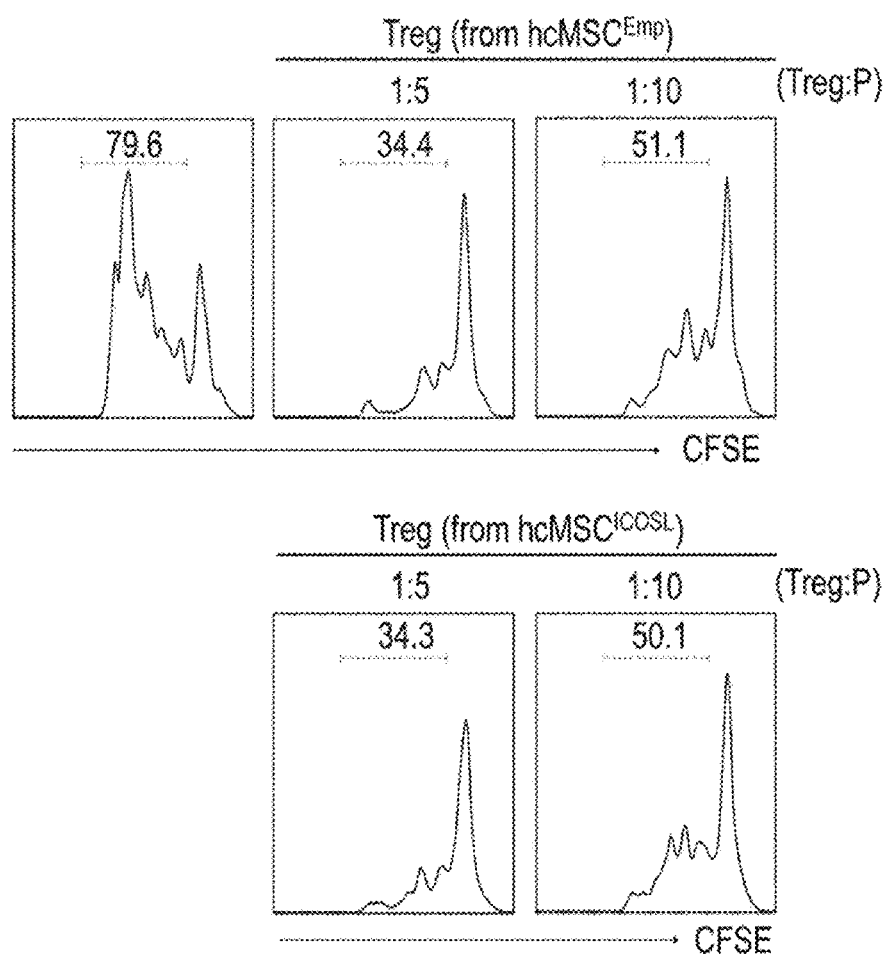
FIG. 12 illustrates the results of analyzing PBMC proliferation after CD25$^+$ populations isolated from co cultures of hcMSC$^{ICOSL}$ or hcMSC$^{Emp}$ were co-cultured with CFSE labeled and activated PBMCs at 1:5 or 1:10 (Treg:PBMC) for 3 days, by CFSE dilution evaluation flow cytometry analyzer.

As illustrated in FIG. 12, CFSE assays revealed that the activated PBMCs were approximately 80% in the absence of Treg. When Treg was co-cultured, dividing PBMCs were decreased in a cell number-dependent manner so that Treg exhibited immune inhibitory effect. Meanwhile, there were no apparent functional differences for PBMC inhibition between hcMSC$^{ICOSL}$-induced and hcMSC$^{Emp}$-induced Tregs.

EXAMPLE 9

Identification of PI3K-Akt Signaling Pathway Activation by ICOSL-ICOS Interaction It has been known that PI3K-Akt signaling pathway plays significant roles in T cell functions such as proliferation, migration, differentiation and cytokine production of T cell. To further define the physiological function of ICOSL, the molecular signaling regulation by ICOSL-ICOS interaction during Treg differentiation was examined in terms of signal transduction.

For this Example, CD4$^+$ T cells were treated with rhICOSL, recombinant human ICOSL (5 μg/mL) (R&D research, Minneapolis, Minn., USA), for 2 days under Treg induction conditions, and their expression of CD25, ICOS and FoxP3 was analyzed by flow cytometry. Five independent experiments were carried out. In particular, for the administration of rhICOSL (R&D research, Minneapolis, Minn., USA), the wells were coated with 5 μg/mL rhICOSL at 37° C. for 4 hours. The purified CD4$^+$ cells were added to each of wells at $1 \times 10^6$ cells/mL, which were stimulated with 1 ng/mL IL-2 (eBiosciences), 5 ng/mL TGF-α (R&D research, Minneapolis, Minn., USA) and 0.1 μM all-trans-retinoic acid (atRA; PHASigma-Aldrich, St. Louis, Mo., USA) as well as 3 μg/mL anti-CD28 mAb (eBiosciences) for 2 to 5 days. hcMSCs were co-cultured with CD4$^+$ T cells at ratio of 1:10 (hcMSCs:T cells) for 2 days. After 2 days, hcMSCs were washed three times with cold phosphate-buffered saline (PBS) containing 0.05 mM ethylenediamine tetraacetic acid (EDTA) to detach lymphocytes from hcMSCs. Then, hcMSCs were trypsinized and washed twice with cold PBS-EDTA solution and stained with phycoerythrin (PE)-conjugated ICOSL antibody (BioLegend) to analyze ICOSL expression. The phosphorylation of Akt by rhICOSL treatment was confirmed by Western blotting. The results are illustrated in FIG. 13.

Figure 13A:
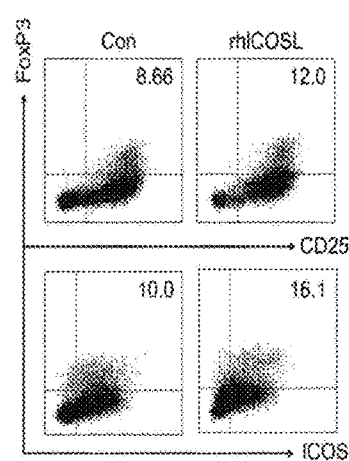
FIGS. 13A-13B illustrate the results of flow cytometry analysis of Treg differentiation induction effects by rhICOSL treatment (A) and results of Western blotting analysis of Akt phosphorylation effect by rhICOSL treatment (B).
Figure 13B:
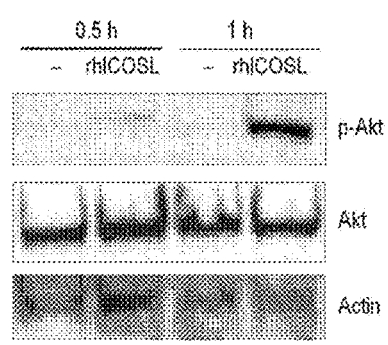

As illustrated in FIG. 13, similar to results of hcMSCs treatment, treatment of rhICOSL in CD4$^+$ T cells also sufficiently promoted FoxP3$^+$ICOS$^+$ Treg induction compared with non-treated control (A). Further, treatment of rhICOSL significantly increased Akt phosphorylation (B). These results reveal that ICOSL activates the PI3K-Akt signaling pathway during Treg induction.

EXAMPLE 10

Identification of Regulation of Treg Differentiation Through PI3K-Akt Signaling Pathway To further demonstrate the involvement of PI3K-Akt signaling pathway in ICOSL-mediated Treg differentiation, they were treated with phosphatidylinositide 3-kinases (PI3K) inhibitor LY294002 or Akt inhibitor GSK690693, and thus their results were confirmed. Akt inhibitor GSK649 (Calbiochem, San Diego, Calif., USA) was used at a concentration of 1 µM and LY294002 (Cell Signaling Technology, Danvers, Mass., USA) was used at concentration of 5 to 10 µM.

More particularly, CD4$^+$ T cells were pre-treated with LY294002 (5 µM) and GSK690693 (1 µM) for 30 min. It was confirmed whether exogenous treatment of rhICOSL induced Akt phosphorylation and whether PI3K-Akt inhibitors inhibited rhICOSL-induced Akt phosphorylation within an hour under Treg induction condition. Total Akt was determined. Further, after treating with LY294002 (5 µM) or GSK690693 (1 µM) for 2 days, rhICOSL-treated CD4$^+$ T cells were incubated to analyze expression of CD25, ICOS and FoxP3, thereby assessing the effects of PI3K-Akt inhibition in the rhICOSL-induced Treg induction. The results are illustrated in FIG. 14.

Figure 14A:
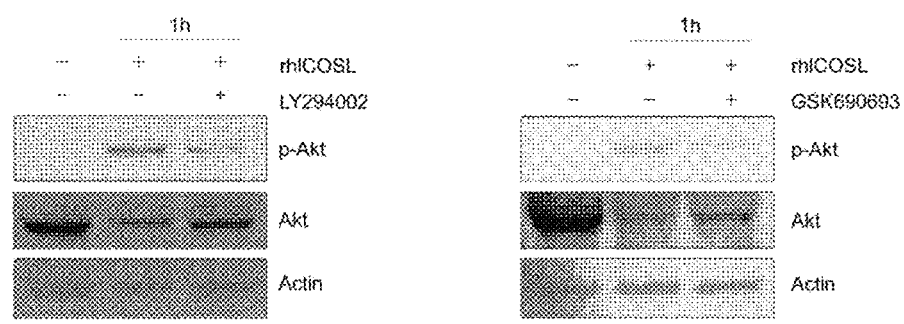
FIGS. 14A-14B illustrate the results of confirming PI3K-Akt phosphorylation inhibitory effect (A) and Treg differentiation inhibitory effect (B) by treatment with the PI3K inhibitor LY294002 (5 µM) and the Akt inhibitor GSK690693 (1 µM) in order to confirm whether PI3K-Akt signaling pathway is involved in ICOSL-mediated Treg differentiation.
Figure 14B:
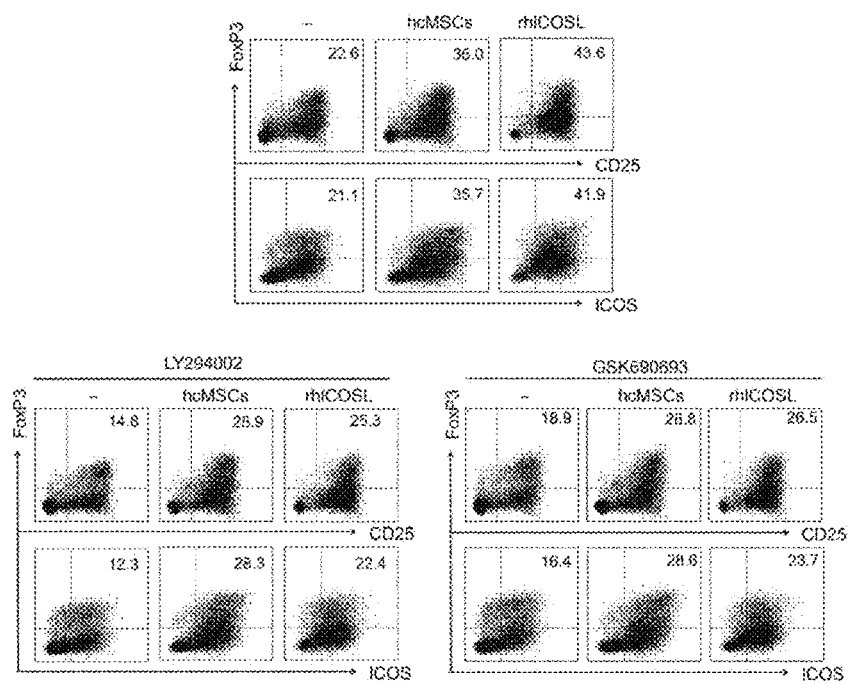
Figure 15A:
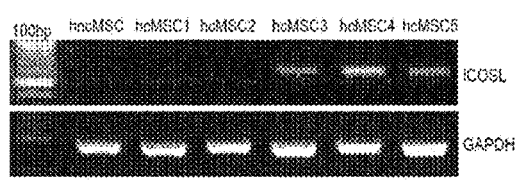
FIGS. 15A-15D illustrate the results of confirming the differences in ICOSL expression between non-clonal MSCs (hncMSC) and hcMSCs 1 to 4 with RT-PCR and qRT-PCR (A and B) and comparison of their Treg cell inducing ability by co-culture with PBMC (C) and under the Treg inducing condition (D) in mixed lymphocyte reaction (MLR).
Figure 15B:
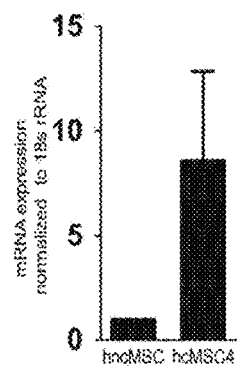
Figure 15C:
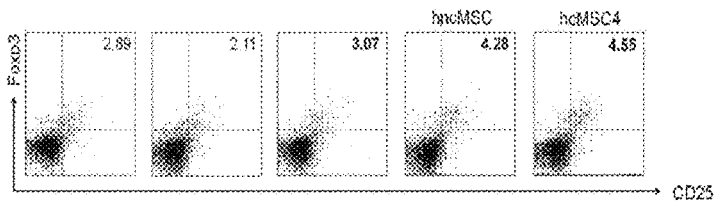
Figure 15D:
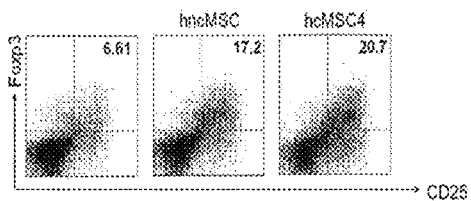

As illustrated in FIG. 14, both LY294002 and GSK690693 treatment resulted in a marked decrease in Akt phosphorylation (A). At the same time, rhICOSL or hcMSC-induced Tregs were decreased by these inhibitors (B). These results demonstrate that the PI3K-Akt signaling pathway is involved in ICOSL-regulated Treg induction. On the other hand, decreased Treg population at normal states by the inhibition of PI3K-Akt pathway indicates the functional importance of this signaling pathway during normal Treg induction (B). These results suggest that the ICOSL-ICOS-PI3K-Akt signaling axis may be involved in the regulation of hcMSC-mediated Treg induction.

EXAMPLE 11

Identification of Correlation Between ICOSL Expression and Treg Induction Among MSC Clones It has been known that different MSC clones exhibit different functional properties. Thus, it was confirmed whether levels of ICOSL expression for inducing human Treg was different according to hcMSC. A total of six hcMSC lines including five clonal hcMSCs (hcMSC1-5) and one non-clonal hcMSC (hncMSC) derived from one donor was examined for their basal expression of ICOSL by Western blotting and qRT-PCR. Further, in order to assess the Treg-inducing activity of hcMSCs, the potential of Treg induction of hcMSC1 and hcMSC4 lines was examined in which expression of CD25 and FoxP3 was compared among hncMSC, hcMSC1 and hcMSC4 by co-culturing each cell line with PBMCs in a mixed lymphocyte reaction (MLR) or in a Treg induction condition. The results are illustrated in FIG. 15.

As illustrated in FIG. 15, it was confirmed that hcMSC4 exhibited the highest ICOSL mRNA expression level of ICOSL, and most hcMSCs showed higher ICOSL expression level compared with hncMSC (A and B). In particular, hcMSC4 showed the highest expression of CD25 and FoxP3 in both MLR condition (C) and Treg induction condition (D). The results confirm that hcMSC4 is the most effective cell line for Treg induction. Further, as cell lines show higher ICOSL mRNA expression, it shows higher Treg induction effects. These results show that the potency of ICOSL expression correlates with the potency of hcMSC for inducing Treg, and the higher the ICOSL inducible cell line, the higher the Treg inducing ability.

EXAMPLE 12

Identification of ICOSL Induction in hcMSC by IL-1β

It has been known that the immunosuppressive activity of MSCs can be influenced by various priming or appropriate stimulations. It was confirmed that ICOSL expression in hcMSCs correlated with Treg induction. Thus, it was expected that ICOSL expression was enhanced to increase Treg and to strengthen the immunosuppressive function of hcMSCs. To confirm this expectation, an experiment was first carried out to confirm pro-inflammatory cytokine that can induce ICOSL expression. First, to find appropriate priming factors, hcMSCs were treated with IL-1β (10 ng/mL), TNF-α (10 ng/mL) and LPS (2 µg/mL) for 24 hours. Then, ICOSL expression was determined after 1 hour and 3 hours though qRT-PCR. Further, in order to confirm whether the expression of IL-1R in hcMSC was changed by IL-10 treatment, the expression of IL-1R in hcMSC was confirmed after treatment with IL-1β for 24 hours. The results are illustrated in FIG. 16.

Figure 16A:
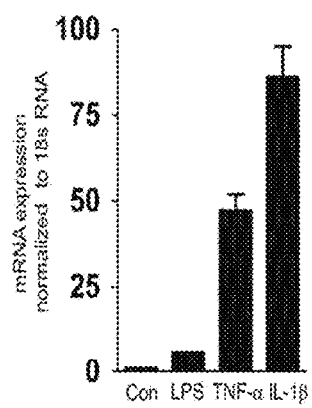
FIGS. 16A-16C illustrate the results of confirming the increase of ICOSL mRNA expression by IL-1β, TNF-α and LPS treatment (A), the increase of ICOSL mRNA expression by IL-1α over time (B) and change on IL-1R expression by IL-1β (C).
Figure 16B:
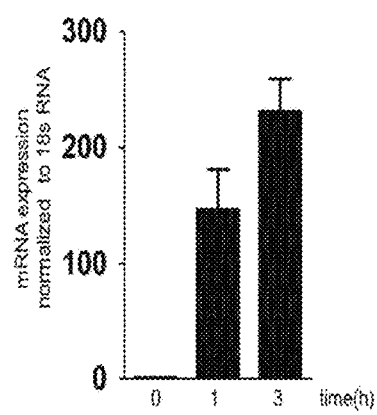
Figure 16C:
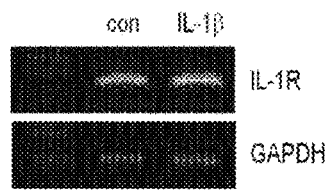

As illustrated in FIG. 16, it was confirmed that the levels of ICOSL mRNA were increased in all IL-10, TNF-α and LPS treatment groups (A and B), and IL-1β among them exhibited the highest effect. It is known that IL-1β binds to its receptor, IL-1R1, to regulate the cellular response, and IL-1R1 is expressed in hcMSC. As the RT-PCR results, it was found that normal hcMSCs expressed IL-1R1 mRNA. Further, treatment with IL-1β (10 ng/ml) immediately and significantly increased ICOLS mRNA but did not change the expression of IL-1R mRNA.

EXAMPLE 13

Identification of IL-1β Inducible Effect by Clonal MSC

It was confirmed that the inducible effect of ICOSL expression was higher in hcMSC4 than in hncMSCs. Thus, experiments were conducted to confirm the difference in ICOSL inducible effects of clonal and non-clonal MSCs by IL-1β treatment. In detail, hcMSC4 and hncMSC were treated with IL-1β (10 ng/ml) for 24 hours, and the expression of ICOSL mRNA was analyzed by qRT-PCR over time. Western blotting and flow cytometry analysis revealed changes in ICOSL protein expression. Flow cytometry indicated a representative value of five independent experiments. The results are illustrated in FIG. 17.

As illustrated in FIG. 17, the qRT-PCR results showed that IL-1β-stimulated ICOSL induction was different between hcMSC4 and hncMSC at both 6 and 24 hours (A). The difference in ICOSL by IL-1β between the two MSCs was identical to Western blotting and flow cytometry analysis (B and C).

IL-1β antibody (10 βg/mL), which is an IL-1β neutralizing antibody, was used to determine whether the difference in ICOSL induction effect was due to IL-1β.

To confirm whether ICOSL inducible effects depending on the kind of clonal and non-clonal MSCs are different due to IL-1β, they were treated with an anti-IL-1β antibody (10 µg/mL), which is an IL-1β neutralizing antibody, to block IL-1β function. Therefore, change in ICOSL inducible effects was determined. The results are illustrated in FIG. 18.

Figure 18:
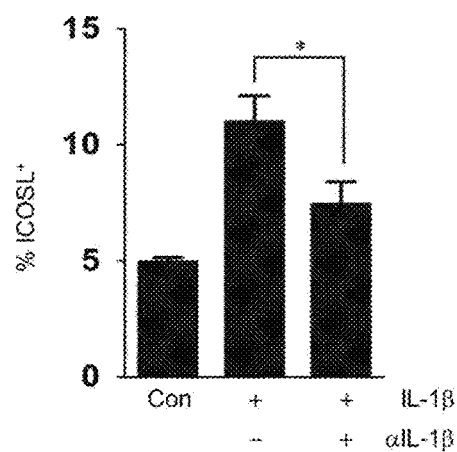
FIG. 18 illustrates the results of confirming the change in the induction of ICOSL expression after IL-1β blockade by treatment with anti-IL-1β neutralizing antibody (*P=0.003).

As illustrated in FIG. 18, treatment of anti-IL-1β neutralizing antibody blocked the function of IL-1β, resulting in decreasing ICOSL expression induced by IL-1β.

These results demonstrate that IL-1β is a potent priming factor to induce ICOSL in hcMSCs.

EXAMPLE 14

Identification of Effect of Increasing Treg Induction by IL-1β Treatment

To examine whether hcMSCs primed with IL-1β exhibited more potent Treg-inducing activity, hcMSCs were treated with IL-1β for 24 hours, thereby obtaining hcMSC$^{IL-1\beta}$. The hcMSC$^{IL-1\beta}$ was co-cultured with CD4$^+$ T cells under Treg differentiation condition. Flow cytometry was performed to confirm a ratio of CD4$^+$CD25$^+$FoxP3$^+$ or CD4$^+$ICOS$^+$Foxp3$^+$ T cell population. Further, after treatment with anti-ICOSL neutralizing antibody (5 ug/ml), hcMSC$^{IL-1\beta}$ was co-cultured with CD4$^+$ T cells to confirm whether ICOS neutralizing inhibition suppressed Treg induction caused by hcMSCs primed with IL-10. The results are illustrated in FIG. 19.

Figure 19A:
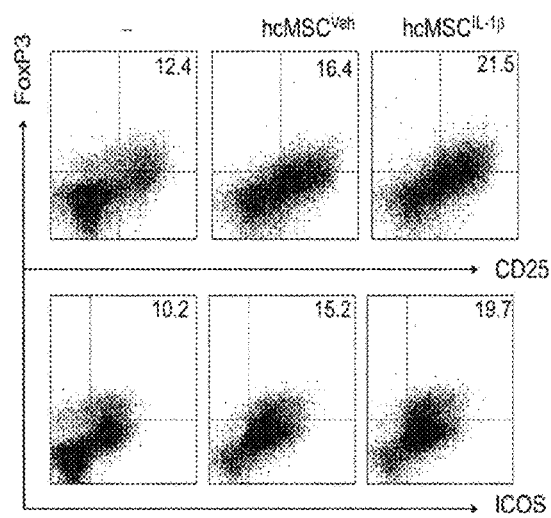
FIG. 19A illustrates the result of flow cytometry analysis on the ratio of CD4$^+$CD25$^+$FoxP3$^+$ or CD4$^+$ICOS$^+$Foxp3$^+$ T cell population by IL-1β priming (hcMSC$^{IL-1\ β}$; IL-1β priming hcMSC, hcMSC$^{Veh}$; IL-1β untreated hcMSC).
Figure 19B:
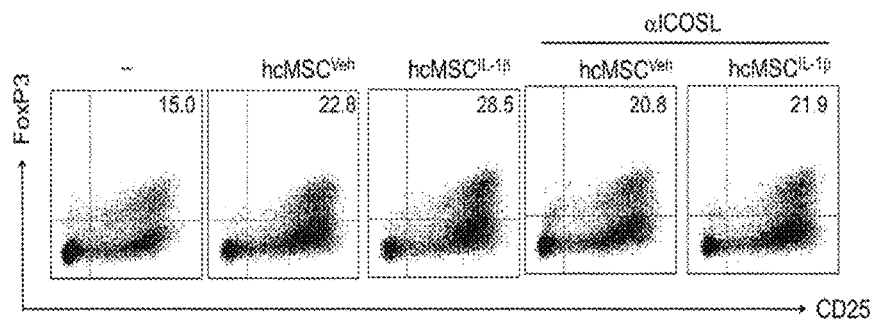
FIG. 19B illustrates the results of confirming the reduction effect of CD25$^+$FoxP3$^+$ Treg induced by hcMSC$^{IL-1\beta}$ and normal hcMSC by anti-ICOSL neutralizing antibody treatment (αICOSL).

As illustrated in FIG. 19, IL-1β-primed hcMSCs (hcMSC$^{IL-1\beta}$) produced more CD25$^+$FoxP3$^+$ Treg compared with hcMSC$^{Veh}$, which is IL-1β-unprimed hcMSC (A). Further, the treatment of anti-ICOSL neutralizing antibody decreased CD25$^+$FoxP3$^+$ Tregs induced both by hcMSC$^{IL-1\beta}$ and normal hcMSC (B). These results demonstrate that hcMSCs primed with IL-1β express ICOSL, which further promotes Treg differentiation by activating PI3K-Akt signaling pathway.

EXAMPLE 15

Alleviation of DSS-Induced Colitis by hcMSC 15.1 Preparation of DSS-Induced Colitis Animal Model and Experimental Method The above Examples confirmed the functional role of human ICOSL for the immunosuppressive ability of hcMSC. Therefore, in order to confirm whether or not such treatment can actually be useful for the treatment of T cell-mediated diseases, it was confirmed that whether MSC administration affected immunosuppressive effect in a colitis model, which is one of T cell-mediated diseases.

Figure 20:
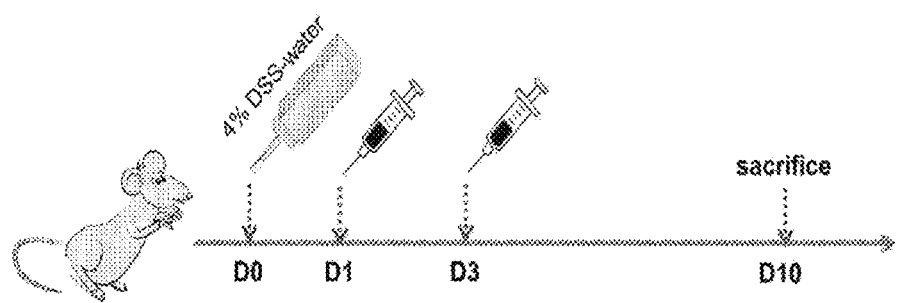
FIG. 20 is a schematic diagram illustrating a method of producing a DSS colitis model.

Acute colitis was induced in Balb/c female mice by administering 4% DSS diluted-drinking water from day 0 to day 7 and changing to regular water from day 8. Balb/c mice were divided into four groups. Such a colitis animal model induction protocol is illustrated in FIG. 20. hcMSCs were transduced by lentivirus expressing ICOSL 24 hours before DSS administration. The transduced hcMSCs were washed with PBS and resuspended at a density of 5×10$^5$ cells/head/200 μl of PBS. At day 1 and 3, hcMSCs (5×10$^5$ cells, 200 μl PBS) were intravenously injected through tail veins. Mice were sacrificed at day 10. Balb/c mice were divided into the following four groups: control group (Con, 4 mice), PBS-treated group with colitis (PBS+DSS, 6 mice) and hcMSC$^{ICOSL}$-transduced group with colitis (hcMSC$^{ICOSL}$+DSS, 6 mice).

15.2 hcMSC Effect on DSS-Induced Colitis

Severity scoring in DSS-induced colitis mouse model was determined daily by evaluating stool consistency, blood and weight loss. The entire colon was removed from the mouse, and colon length was measured as indirect inflammation markers. For analysis of mouse Tregs in the colon, cells isolated from mesenteric lymph nodes were incubated with APC-conjugated anti-CD25, FITC-conjugated anti-CD4 and PE-conjugated anti-FoxP3 antibodies (eBioscience). For in vitro experiment, CD4$^+$ T cells were removed from spleen and lymph nodes. The purity of the isolated cells was determined by flow cytometric analysis. CD4$^+$ T cells were activated with 1 μg/mL plate-bound anti-CD3 mAb and 3 μg/mL soluble anti-CD28 mAb and analyzed at day 1 and day 2. The results are illustrated in FIG. 21.

Figure 21:
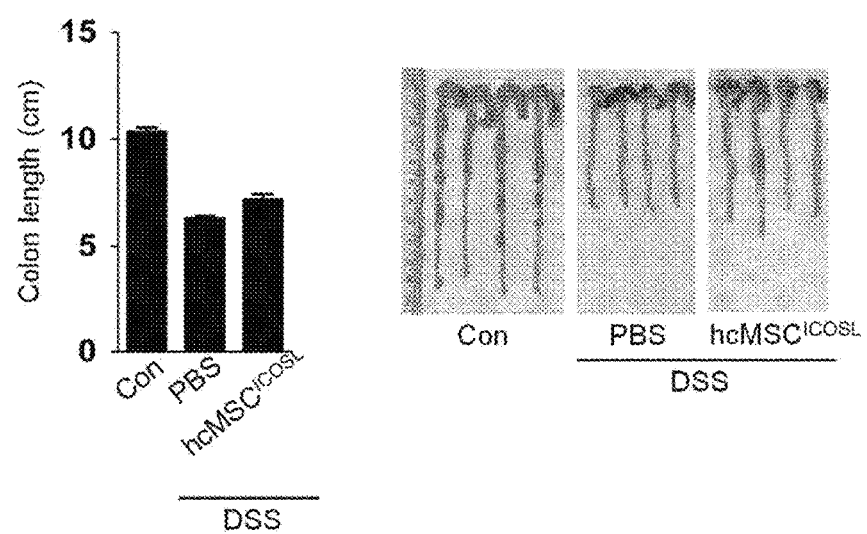
FIG. 21 illustrates the results of confirming the change in the colon length according to the hcMSC$^{ICOSL}$ treatment in the DSS-induced colitis mouse model.

As illustrated in FIG. 21, it was confirmed that hcMSC$^{ICOSL}$-transduced mice had less colon shrinkage compared to PBS-treated mice. Further, hcMSC-transduced mice had less weight loss. These results demonstrate that all hcMSCs$^{ICOSL}$ show colitis relief and therapeutic effects on mice having colitis.

In summary of the results as described above, it indicates that ICOS-ICOSL interaction may play an essential role in human Treg induction by MSCs. Under inflammatory conditions, hcMSCs may induce ICOSL expression on their surface, which may promote induction of Tregs by activating PI3K-Akt signaling pathway through interaction with ICOS expressed on Tregs. IL-1β is a potent priming factor to enhance human Tregs by up-regulating ICOSL in hcMSCs. From these results, it is possible to clearly understand the immunosuppressive mechanism of hcMSC, and to be used for development of a more effective stem cell therapeutic agent for target treatment of intractable immune diseases.

Preparation Example 1

Preparation of Medicines 1.1 Preparation of Powder
ICOSL: 100 mg
Lactose: 100 mg
Talc: 10 mg
The components are mixed and packed in an airtight bag to prepare powders.
1.2 Preparation of Tablet
ICOSL: 100 mg
Cornstarch: 100 mg
Lactose: 100 mg
Magnesium Stearate: 2 mg
The components are mixed and tableted according to a conventional tablet preparation to prepare tablets.
1.3 Preparation of Capsule
ICOSL: 100 mg
Cornstarch: 100 mg
Lactose: 100 mg
Magnesium stearate: 2 mg
The components are mixed and filled in gelatin capsules according to a conventional capsule preparation to prepare capsules.
1.4 Preparation of Injection Agent
ICOSL: 100 mg
Sterile distilled water for injection: suitable amount
pH regulator: suitable amount
Injection agent is prepared to include the above components per 1 ampoule (2 ml) according to a conventional injection preparation.
1.5 Preparation of Liquid Agent
ICOSL: 100 mg
Sugar: 20 g
Isomerized sugar: 20 g
Lemon flavoring: suitable amount Purified water was added to adjust the total volume to 1.00 ml. The above components are mixed according to a conventional liquid agent preparation, then filled in a brown bottle and sterilized to prepare liquid agents.

The invention claimed is:

1. A method for treating a regulatory T cell-mediated disease, the method comprising:
administering an induced T cell co-stimulator ligand (ICOSL)-overexpressing mesenchymal stem cell to an individual.

2. The method of claim 1, wherein the mesenchymal stem cell is a clonal stem cell.

3. The method of claim 1, wherein the mesenchymal stem cell is a bone marrow-derived mesenchymal stem cell.

4. The method of claim 1, wherein the ICOSL increases expression of an inducible T cell co-stimulator (ICOS) of a T cell.

5. The method of claim 1, wherein the ICOSL activates a signal pathway of PI3K (phosphoinositide 3-kinase)-Akt.

6. The method of claim 1, wherein the mesenchymal stem cell is treated with one or more selected from the group consisting of IL-1β, TNF-α, IL-6, IL-2, IL-1, and LPS (lipopolysaccharide).

7. The method of claim 1, wherein the regulatory T cell-mediated disease is an inflammatory disease or autoimmune disease.

8. The method of claim 7, wherein the inflammatory disease includes one or more selected from the group consisting of lupus, Sjogren's syndrome, rheumatoid arthritis, fibromyositis, scleroderma, ankylosing spondylitis, Behcet's disease, aphthous stomatitis, Guillain Barre syndrome, alopecia areata, dermatomyositis, Crohn's disease, colitis, polyarteritis *nodosa*, relapsing polychondritis and autoimmune thrombocytopenia.

9. The method of claim 7, wherein the autoimmune disease includes one or more selected from the group consisting of rheumatoid arthritis, systemic scleroderma, insulin-dependent childhood diabetes mellitus due to pancreatic cell, areata alopecia, psoriasis, pemphigus, asthma, aphthous stomatitis, chronic thyroiditis, partial acquired aplastic anemia, primary hepatocirrhosis, ulcerative colitis, Behcet's disease, Crohn's disease, silicosis, asbestosis, IgA kidney disease, poststreptococcal glomerulonephritis, Sjogren's syndrome, Guillain Barre syndrome, dermatomyositis, polymyositis, multiple sclerosis, autoimmune hemolytic anemia, autoimmune encephalomyelitis, myasthenia gravis, Grave's thyroid hyperplasia, nodular polyarteritis, ankylosing spondylitis, fibrositis, temporal arteritis, Wilson's disease, Pakoni's syndrome, multiple myeloma and systemic lupus erythematosus.

10. A method for inducing differentiation and proliferation of a CD4+ T cell into a regulatory T cell, the method comprising:
treating a CD4+ T cell in vitro with an induced T cell co-stimulator ligand (ICOSL) or an ICOSL-overexpressing mesenchymal stem cell.

11. The method of claim 10, wherein the ICOSL-overexpressing mesenchymal stem cells are pre-treated with one or more selected from the group consisting of IL-1β, TNF-α, IL-6, IL-2, IL-1, and LPS (lipopolysaccharide).

* * * * *

```
                       SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: IL-10 Forward primer

<400> SEQUENCE: 1
atccaagaca acactactaa                                              20

<210> SEQ ID NO 2
<211> LENGTH: 19
<212> TYPE: DNA
<213> ORGANISM: Artificial Sequence
<220> FEATURE:
<223> OTHER INFORMATION: IL-10 reverse primer

<400> SEQUENCE: 2
taaatatcct caaagttcc                                               19

<210> SEQ ID NO 3
<211> LENGTH: 20
<212> TYPE: DNA
<213> ORGANISM: Artificial Sequence
<220> FEATURE:
<223> OTHER INFORMATION: IL-1  forward primer

<400> SEQUENCE: 3
gctgagtgct gcaaagtacc                                              20

<210> SEQ ID NO 4
<211> LENGTH: 20
<212> TYPE: DNA
<213> ORGANISM: Artificial Sequence
<220> FEATURE:
<223> OTHER INFORMATION: IL-1  reverse primer

<400> SEQUENCE: 4
tgaggaggga cttgtgactg                                              20

<210> SEQ ID NO 5
<211> LENGTH: 20
<212> TYPE: DNA
<213> ORGANISM: Artificial Sequence
<220> FEATURE:
<223> OTHER INFORMATION: IL-1R forward primer

<400> SEQUENCE: 5
attgatgttc gtccctgtcc                                              20

<210> SEQ ID NO 6
<211> LENGTH: 20
<212> TYPE: DNA
<213> ORGANISM: Artificial Sequence
<220> FEATURE:
<223> OTHER INFORMATION: IL-1R reverse primer

<400> SEQUENCE: 6
cctccacctt agcaggaaca                                              20

<210> SEQ ID NO 7
```

```
<211> LENGTH: 19
<212> TYPE: DNA
<213> ORGANISM: Artificial Sequence
<220> FEATURE:
<223> OTHER INFORMATION: GAPDH forward primer

<400> SEQUENCE: 7
ccactggcgt cttcaccac                                                 19

<210> SEQ ID NO 8
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 8
cctgcttcac caccttcttg                                                20
```